(12) United States Patent
Fein et al.

(10) Patent No.: US 6,490,466 B1
(45) Date of Patent: Dec. 3, 2002

(54) INTERCONNECT CIRCUIT BETWEEN NON-COMPATIBLE OXIMETER AND SENSOR

(75) Inventors: Michael E. Fein, Mountain View, CA (US); Bradford B. Chew, San Ramon, CA (US)

(73) Assignee: Mallinckrodt Inc., Hazelwood, MO (US)

( * ) Notice: Subject to any disclaimer, the term of this patent is extended or adjusted under 35 U.S.C. 154(b) by 58 days.

(21) Appl. No.: 09/668,032

(22) Filed: Sep. 21, 2000

(51) Int. Cl.[7] .................................................. A61B 5/00
(52) U.S. Cl. ........................ 600/323; 600/322; 600/331
(58) Field of Search ................................. 600/309–324; 385/20; 439/488–489, 620–622; 356/39–42

(56) References Cited

U.S. PATENT DOCUMENTS

| | | | |
|---|---|---|---|
| 4,700,708 A | | 10/1987 | New, Jr. et al. |
| 5,124,673 A | * | 6/1992 | Hershberger ............... 333/18 |
| 5,196,833 A | * | 3/1993 | Kemp ....................... 340/663 |
| 5,209,230 A | | 5/1993 | Swedlow et al. |
| 5,249,576 A | | 10/1993 | Goldberger et al. |
| 5,758,644 A | | 6/1998 | Diab et al. |
| 5,807,247 A | | 9/1998 | Merchant et al. |
| 5,818,985 A | * | 10/1998 | Merchant et al. ............. 385/20 |
| 5,987,343 A | * | 11/1999 | Kinast ....................... 600/323 |
| 5,995,855 A | * | 11/1999 | Kiani et al. ................. 600/310 |
| 5,997,343 A | * | 12/1999 | Mills et al. ................. 439/489 |
| 6,023,541 A | | 2/2000 | Merchant et al. |

* cited by examiner

Primary Examiner—Eric F. Winakur
Assistant Examiner—Matthew Kremer
(74) Attorney, Agent, or Firm—Townsend and Townsend and Crew LLP

(57) ABSTRACT

An oximeter sensor adapter which allows a sensor without a resistor in parallel with its LEDs to operate with an oximeter expecting such a resistor in parallel. The adapter has a switching circuit which has inputs connected to the LED drive outputs of the oximeter. The switching circuit has two pairs of outputs, one connected to the LED drive lines of the sensor, and the other connected to a resistor in the adapter itself. The switching circuit is controlled by a sensing circuit which senses when a signal on the input lines drops below a predetermined level, such as 0.5 volts. The sensing circuit, in response to a low voltage (corresponding to an attempt to read a resistor in parallel with the LEDs), will provide a signal to a switching circuit. The switching circuit will switch the resistor onto the input lines so that it can be read. When a higher voltage returns to the input lines, the switching circuit switches back to the LEDs themselves.

11 Claims, 2 Drawing Sheets

INTERCONNECT CIRCUIT BETWEEN NON-COMPATIBLE OXIMETER AND SENSOR

BACKGROUND OF THE INVENTION

This invention relates in general to optical oximeters and relates more particularly to an adapter that enables an optical oximeter probe, that is designed/configured to be utilized on an associated oximeter/monitor, to be used on a different oximeter/monitor that utilizes a different probe configuration.

Because of the importance of oxygen for healthy human metabolism, it is important to be able to measure the oxygen content of a patient's blood. The monitoring of a patient's arterial hemoglobin oxygen saturation during and after surgery is particularly critical.

Noninvasive oximeters have been developed that direct light through a patient's skin into a region, such as a finger, containing arterial blood. This light typically contains two or more primary wavelengths of light. Examples of such oximeters are disclosed in U.S. Pat. No. 5,209,230 entitled "Adhesive Pulse Oximeter Sensor With Reusable Portion" issued to Swedlow, et al. and in U.S. Pat. No. 4,700,708 entitled "Calibrated Optical Oximeter Probe" issued to New, Jr. et al., both assigned to the assignee of the present invention, the disclosures of which are incorporated herein by reference. The oximeter in the patent by New, Jr. et al. includes a probe that contains a resistor having a resistance that can be measured by a monitor to which the probe is attached. The measured value of this resistance is indicative of the wavelengths of the light directed from the light emitting diodes (LEDs) through the patient's epidermis. The monitor uses this information and the measured intensities of light detected at those wavelengths to calculate the blood arterial oxygen content of the patient. The LEDs are typically activated in non-overlapping temporal intervals, so that the amount of absorption of light at each of these two wavelengths is usually measured separately.

Oftentimes, an oximeter sensor may be made by one manufacturer, and a monitor by another manufacturer. Accordingly, adapters may be necessary if the sensor and the oximeter/monitor are not compatible. Alternately, the sensor itself can be configured so that it can be used with different oximeters. For example, U.S. Pat. No. 5,249,576, entitled "Universal Pulse Oximeter Probe" issued to Goldberger et al., allows the leads of the sensor to be connected in alternate configurations. Examples of adapters are set forth in U.S. Pat. No. 5,807,247, assignee Nellcor Puritan Bennett, Inc., and in U.S. Pat. No. 5,818,985, also assigned to Nellcor Puritan Bennett, Inc. Yet another adapter is set forth in copending application No. 09/040,218, filed Mar. 17, 1998, entitled "Active Optical Oximeter Probe Adapter", Adnan Merchant et al., also assigned to Nellcor Puritan Bennett, Inc. The disclosures of all three of the above Nellcor Puritan Bennett applications are incorporated herein by reference.

In one type of oximeter sensor, set forth in Masimo Corporation U.S. Pat. No. 5,758,644, separate leads on the sensor for connecting to a coding resistor are eliminated. Instead, the coding resistor is connected in parallel with the light-emitting diodes (LEDs) of the sensor. The coding resistor can be read by providing a low voltage at which the LEDs will not conduct substantial current. For example, a voltage of 0.5 volts will accomplish this. Thus, in a configuration mode, a low voltage can be driven to the LED leads, and the resistance can be read. Subsequently, higher voltages can be used for driving the LEDs in an operational mode. Clearly, oximeter sensors without such a resistance across the LED leads will not be compatible with such an arrangement. In one embodiment of the Masimo sensor, the resistor does not provide a coding function at all, but rather modifies the characteristics of the LEDs.

SUMMARY OF THE INVENTION

The present invention provides an oximeter sensor adapter which allows a sensor without a resistor in parallel with its LEDs to operate with an oximeter expecting such a resistor in parallel. The adapter has a switching circuit which has inputs connected to the LED drive outputs of the oximeter. The switching circuit has two pairs of outputs, one connected to the LED drive lines of the sensor, and the other connected to a resistor in the adapter itself. The switching circuit is controlled by a sensing circuit which senses when a signal on the input lines drops below a predetermined level, such as 0.5 volts. The sensing circuit, in response to a low voltage (corresponding to an attempt to read a resistor in parallel with the LEDs), will provide a signal to a switching circuit. The switching circuit will switch the resistor onto the input lines so that it can be read. When a higher voltage returns to the input lines, the switching circuit switches back to the LEDs themselves.

Thus, the present invention in essence fools the oximeter into thinking that there is a resistor connected in parallel with the LEDs, when in fact there is not. It allows a sensor without a resistor across its LED leads to work with an oximeter expecting such a resistor.

For a further understanding of the nature and advantages of the invention, reference should be made to the following description taken in conjunction with the accompanying drawings.

DESCRIPTION OF THE SPECIFIC EMBODIMENTS

Figure 1:
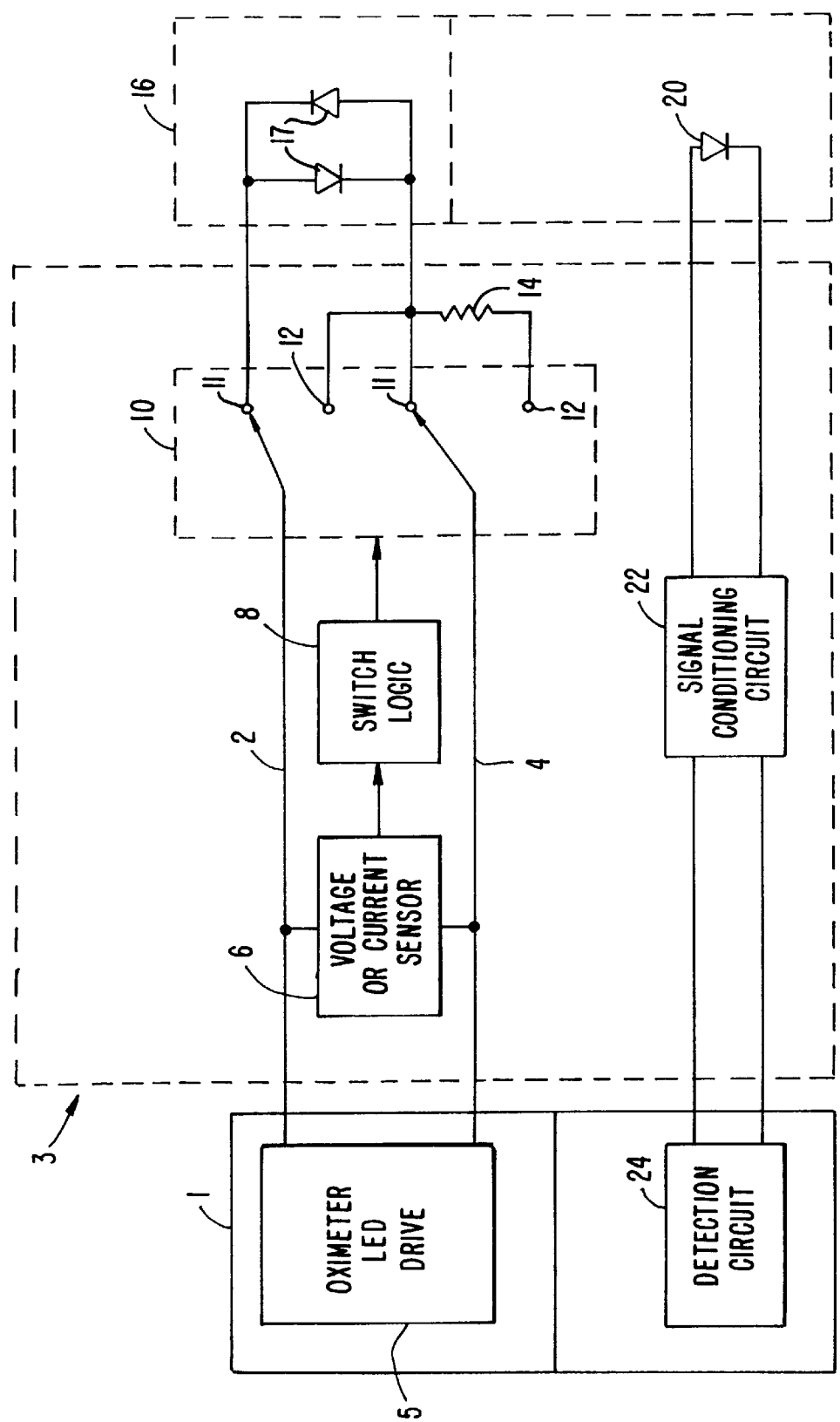
FIG. 1 is a block diagram of an oximeter system with an adapter according to the present invention.

FIG. 1 is a block diagram of one embodiment of an adapter according to the present invention in an oximeter system. Shown in FIG. 1 is a pulse oximeter 1, an adapter 3, and a sensor or probe 16. The sensor includes LEDs 17 for directing light into the patient, typically red and infrared. The LEDs are driven by an oximeter LED drive circuit 5 in oximeter 1. This drive signals onto lines 2 and 4 through adapter 3. Lines 2 and 4 are connected through a switching circuit 10 to contacts 11 which are connected to the LEDs 17. This is the normal, operational configuration of the system.

When it is desired to read a resistance upon calibration, oximeter drive circuit 5 will put out a low voltage signal which is too low to produce any significant current through LEDs 17. Typically, this voltage will be around 0.5 volts. This low voltage is sensed by a voltage sensing circuit 6. Circuit 6 then provides a signal through switch logic 8 to switching circuit 10 to cause the switch to move to contacts 12 from contacts 11. Contacts 12 put lines 2 and 4 across resistor 14. Thus, the 0.5 volt signal from LED drive circuit 5 will be applied across resistor 14, and the value of resistor 14 can be read by the oximeter. Once the reading is completed, and the oximeter desires to drive the LEDs in the normal mode, a higher voltage signal will appear across lines 2 and 4. This will also be detected by sensor 6, which will cause switch logic 8 to switch switching circuit 10 back to contacts 11.

The oximeter sensor also has a photosensor 20 for detecting light transmitted through or reflected from the patient. Sensor 20 is connected through adapter 3 through an optional signal conditioning circuit 22 and then provided to a detection circuit 24 in oximeter 1.

Figure 2:
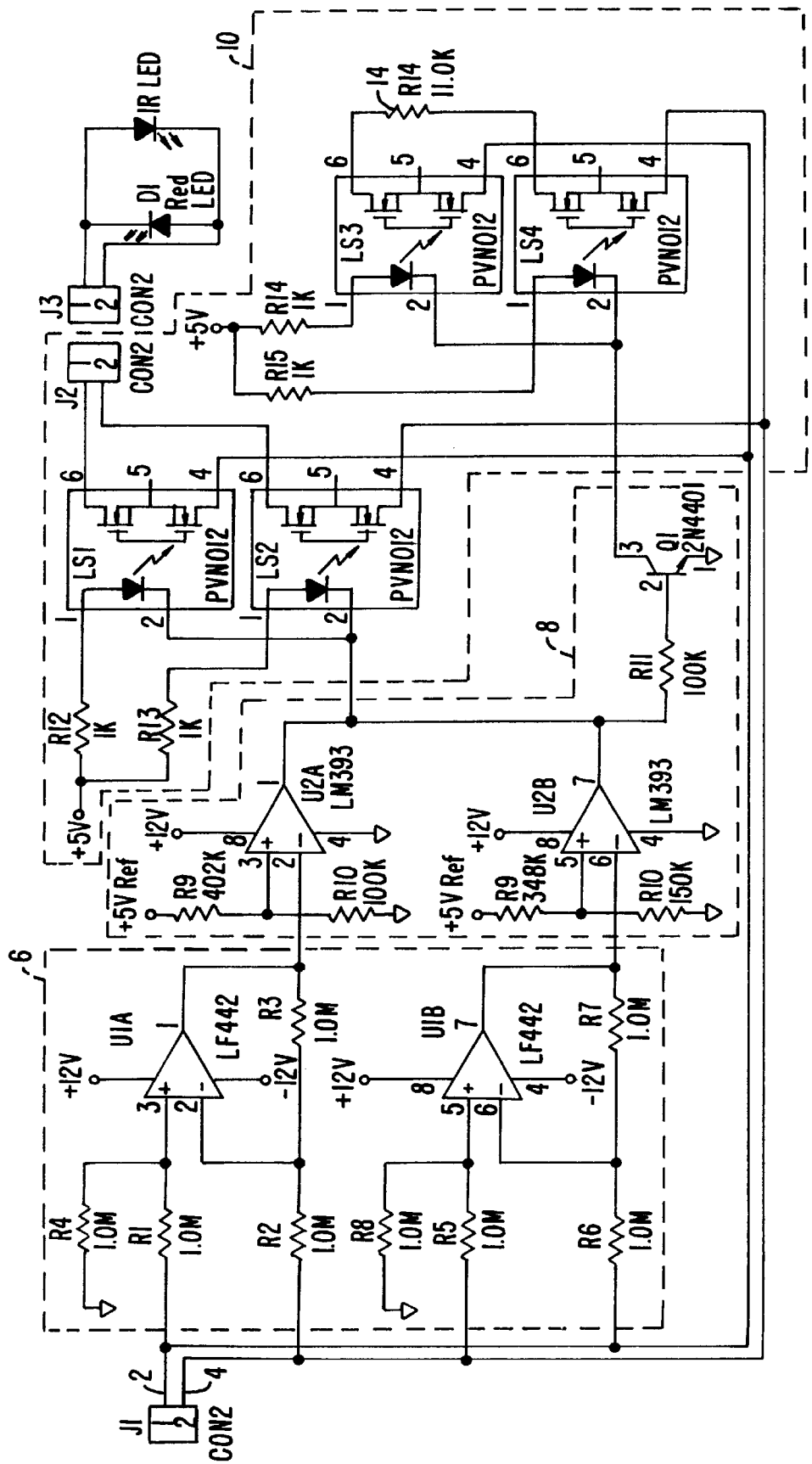
FIG. 2 is a more detailed diagram of one embodiment of voltage sensor 6, switching logic 8 and the sensing circuit 10 of the adapter of FIG. 1.

FIG. 2 is a more detailed diagram of one embodiment of voltage sensor 6, switching logic 8 and switching circuit 10 of FIG. 1. In this example, a voltage sensor causes the switch to disconnect the 11K coding resistor if the IR LED forward voltage exceeds 1.0V, (connecting the IR LED) and if the Red LED forward voltage exceeds 1.5V, (connecting the Red LED).

OpAmps U1A and U1B function as differential amplifiers, where V(U1A)=V(2)−V(4), and V(U1B)=V(4)−V(2). The outputs of U1A and U1B are compared to their threshold voltages at comparators U2A (IR threshold at 1.0V) and U2B (Red threshold at 1.5V). Both comparators have open collector outputs, so if either V(U1A) or V(U1B) exceeds its threshold, the output is pulled low, activating optical switches LS1 and LS2, connecting both LEDs to lines 2 and 4. If U2A or U2B pull their common line low, transistor Q1 turns off, which turns off optical switches LS3 and LS4 and disconnects resistor 14 from lines 2 and 4.

If the oximeter tries to measure resistor 14 with the 0.5 volt signal, both V(U1A) and V(U1B) will be below threshold and comparator outputs of U2A and U2B will be pulled high by resistors R12 and R13, deactivating optical switches LS1 and LS2, disconnecting both LEDs from lines 2 and 4. This also turns on transistor Q1, which turns on optical switches LS3 and LS4, and connects resistor 14 to lines 2 and 4.

Optional signal conditioning circuit 22 of FIG. 1 is used to change the photo-detected signal to correspond to the type of sensor 16 actually used. For example, the relationship between R (the ratio of ratios) and SpO$_2$ may be altered by varying the photo-detected signal level. An example of such a circuit is set forth in copending application Ser. No. 09/040,218, filed Mar. 17, 1998, referenced above and incorporated herein by reference.

Referring back to FIG. 1, in other embodiments, instead of a resistor 14, another element may be used to convey information or unlock the oximeter to allow use of the sensor. For example, a semiconductor chip providing digital data may be used to provide more complex coding information than a simple resistor can provide. Such a chip could be a two lead memory chip, such as is available from Dallas Semiconductor.

The adapter itself may have its separate power supply, or may operate off the power provided by oximeter 1. For the calibration mode, the adapter could store energy from the LED drives.

As will be understood by those of skill in the art, the present invention may be embodied in other specific forms without departing from the essential characteristics thereof. For example, a three lead connection for the LEDs in the sensor could be used, with the voltage sensing and switching logic modified accordingly. The adapter could convert from a 3 lead oximeter to a 2 lead sensor, or vice-versa. Accordingly, the foregoing description is intended to be illustrative, but not limiting, of the scope of the invention which is set forth in the following claims.

What is claimed is:

1. An oximeter sensor adapter, comprising:
   a pair of first and second oximeter input lines connectable to oximeter LED drive output lines;
   a pair of sensor output lines connectable to LED drive input lines of an oximeter sensor;
   a sensing circuit, coupled to said first and second oximeter input lines, to detect when a signal on said first input line exceeds a first predetermined level and when a signal on said second input line exceeds a second predetermined level;
   a coding element; and
   a switching circuit, having a control input connected to said sensing circuit, having a first pair of switch inputs coupled to said first and second oximeter input lines, a first pair of switch outputs connected to said sensor output lines, a second pair of switch outputs coupled to said coding element, and being configured to switch between said first and second pairs of switch outputs in response to a signal on said control input.

2. The oximeter sensor adapter of claim 1 wherein said coding element is a resistor.

3. The oximeter sensor adapter of claim 2 wherein said signal on said first input line is a signal below a predetermined voltage.

4. The oximeter sensor adapter of claim 3 wherein said predetermined voltage is 0.5 volts.

5. The oximeter sensor adapter of claim 2 wherein said sensing circuit provides an activating signal to said switching circuit when a voltage on said oximeter input lines is 0.5 volts or less, said activating signal causing said switching circuit to switch to said resistor.

6. The oximeter sensor adapter of claim 2 wherein said resistor has a value related to a value of an LED in an attached sensor.

7. The oximeter sensor adapter of claim 1 wherein said coding element is a semiconductor chip.

8. The oximeter sensor adapter of claim 1 wherein said sensing circuit comprises:
   at least one differential amplifier coupled to said input lines; and
   at least one comparator coupled to an output of said differential amplifier.

9. The oximeter sensor adapter of claim 1 wherein said switching circuit comprises:
   at least first and second optical switches.

10. The oximeter sensor adapter of claim 1 further comprising:
   a conditioning circuit, coupled between a sensor detector line and an oximeter detector line, for varying a photo-detected signal level.

11. An oximeter system comprising:
   (a) an oximeter including
      an LED drive circuit, with a pair of LED drive output lines;
      a photodetector sensor circuit, connected to a photodetector input line; and
   (b) an oximeter sensor adapter, including
      a pair of first and second oximeter input lines connectable to oximeter LED drive output lines;
      a pair of sensor output lines connectable to LED drive input lines of an oximeter sensor;
      a sensing circuit, coupled to said first and second oximeter input lines, to detect when a signal on said first input line exceeds a first predetermined level and when a signal on said second input line exceeds a second predetermined level;

a coding element; and a switching circuit, having a control input connected to said sensing circuit, having a first pair of switch inputs coupled to said first and second oximeter input line, a first pair of switch outputs connected to said sensor output lines, a second pair of switch outputs coupled to said coding element, and being configured to switch between said first and second pairs of switch outputs in response to a signal on said control input.

* * * * *